(12) United States Patent
Kalafatis et al.

(10) Patent No.: US 7,074,892 B2
(45) Date of Patent: Jul. 11, 2006

(54) THROMBIN GENERATION INHIBITORS

(75) Inventors: Michael Kalafatis, Shaker Heights, OH (US); Kenneth G. Mann, Grand Isle, VT (US)

(73) Assignee: Cleveland State University, Cleveland, OH (US)

( * ) Notice: Subject to any disclaimer, the term of this patent is extended or adjusted under 35 U.S.C. 154(b) by 23 days.

(21) Appl. No.: 10/795,795

(22) Filed: Mar. 8, 2004

(65) Prior Publication Data

US 2004/0186271 A1 Sep. 23, 2004

Related U.S. Application Data

(62) Division of application No. 09/911,129, filed on Jul. 23, 2001, now Pat. No. 6,703,364.

(51) Int. Cl.
*A61K 38/08* (2006.01)
*A61K 38/07* (2006.01)
*A61K 38/00* (2006.01)
*A61K 35/14* (2006.01)

(52) U.S. Cl. ............ 530/328; 530/329; 530/330; 530/331; 530/332; 530/380; 514/15; 514/16; 514/17; 514/18

(58) Field of Classification Search ........ 530/328–332, 530/380; 514/15–18
See application file for complete search history.

(56) References Cited

U.S. PATENT DOCUMENTS 6,165,737 A * 12/2000 Wang et al. .............. 435/7.6
6,703,364 B1 3/2004 Kalafatis et al.

FOREIGN PATENT DOCUMENTS

GB         9916529     *   7/1999
WO      WO 9500633 A2  *   1/1995

OTHER PUBLICATIONS

Duve et al. Isolation, sturcture, and activity of -Phe-Met-Arg-Phe-NH2 neuropeptide ( designated calliFNMRamides) from the blowfly *Calliphora vomitoria*. Proceedings of the National Academies of Science, USA. Mar. 1992. vol. 89, pp. 2326-2330.*

"Peptide inhibitors expressed *in vivo*" by Kamb, et al., *Curr. Opin. Chem. Biol.* Feb. 2001; 5(1):74-7.

"Characterization of the Molecular Defect in Factor $V^{R506Q}$" by Kalafatis, et al., *The Journal of Biological Chemistry*, vol. 270, No. 8, Feb. 24, 1995, pp. 4053-4057.

"The Regulation of Clotting Factors" by Kalafatis, et al., *Critical Reviews in Eukaryotic Gene Expression*, 7(3):241-280(1997).

"Role of the Membrane in the Inactivation of Factor Va by Activated Protein C*" by Kalafatis, et al., *The Journal of Biological Chemistry*, vol. 268, No. 36, Dec. 25, 1993, pp. 27246-27257.

"Proteolytic alterations of membrane-bound factor Va during inactivation by plasmin" by Kalafatis, et al., 1997, Abstract No. PS-2503 at scientific meeting.

"The Role of the Membrane in the Inactivation of Factor Va by Plasmin" by Kalafatis, et al., *The Journal of Biological Chemistry*, vol. 276, No. 21, May 25, 2001, pp. 18614-18623.

"Binding Site for Blood Coagulation Factor Xa Involving Residues 311-325 in Factor Va*" by Kojima, et al., *The Journal for Biological Chemistry*, vol. 273, No. 24, Jun. 12, 1998, pp. 14900-14905.

(Continued)

Primary Examiner—Robert A. Wax
Assistant Examiner—Suzanne M. Noakes
(74) *Attorney, Agent, or Firm*—Calfee, Halter and Griswold LLP

(57) ABSTRACT

Peptides derived from amino acids 307 to 356 of the human blood coagulation factor Va are provided. Such peptides comprise: i) a length of between 3 and 50 amino acids, ii) a minimum of 3 contiguous amino acids from the 307–356 heavy chain region of factor Va, excluding peptide segments comprising amino acids 311 to 325 and amino acids 321 to 335, iii) optional additional amino acids at one or both ends of the contiguous amino acids such that the entire peptide is at least 60% identical to a sequence within 307 to 356 of factor Va, and iv) have an $IC_{50}$ of between 50 nM to 500 μM for inhibition of prothrombinase. The present invention also provides a pharmaceutical composition comprising one or more prothrombinase-inhibiting peptide segments. The present invention also provides administration of the pharmaceutical composition to human subjects for the purpose of preventing thrombotic disorders.

9 Claims, 6 Drawing Sheets

OTHER PUBLICATIONS

"Proteolytic processing of human coagulation factor IX by plasmin" by Samis, et al., *Blood*, vol. 95, No. 3, Feb. 1, 2000, pp. 943-951.

"Inhibitory Mechanism of the Protein C Pathway on Tissue Factor-Induced Thrombin Generation" by van't Veer, et al., *The Journal of Biological Chemistry*, vol. 272, No. 12, Mar. 21, 1997, pp. 7983-7994.

"Importance of individual activated protein C cleavage site regions in coagulation Factor V for Factor Va Inactivation and for Factor Xa activation" by Heeb, et al., *Eur. J. Biochem.*, 260, 64-75(1999).

"The Structure and Function of Murine Factor V and Its Inactivation by Protein C" by Yang, et al., *Blood*, vol. 91, No. 12, Jun. 15, 1998, pp. 4593-4599.

* cited by examiner

```
       307 NLKKITREQRRHMKRWEYFIAAEEVIWDYAPVIPANMDKKYRSQHLDNFS 356  SEQ ID NO. 1
NR42       NLKKITREQRRHMKRWEYFIAAEEVIWDYAPVIPANMDKKYR            SEQ ID NO. 2
AP1        NLKKITREQR                                            SEQ ID NO. 3
AP2            TREQRRHMKR                                        SEQ ID NO. 4
AP3              RHMKRWEYFI                                      SEQ ID NO. 5
AP4                  WEYFIAAEEV                                  SEQ ID NO. 6
AP5                      AAEEVIWDYA                              SEQ ID NO. 7
AP6                          IWDYAPVIPA                          SEQ ID NO. 8
AP7                              PVIPANMDKK                      SEQ ID NO. 9
AP8                                  NMDKKYRSQH                  SEQ ID NO. 10
AP9                                      YRSQHLDNFS              SEQ ID NO. 11
L5S                                          LDNFS               SEQ ID NO. 12
Pentapeptide               EYFAE                                 SEQ ID NO. 13
P15H                             PVIPANMDKKYRSQH                 SEQ ID NO. 14
                    ---------------------
VP311        ITREQRRHMKRWEYF                                     SEQ ID NO. 15
VP321              RWEYFIAAEEVIWDY                               SEQ ID NO. 16
                    ---------------------
DR13    697 DADSDYQDELALI 709                                    SEQ ID NO. 17
```

Figure 2

SEQUENCE LISTING

```
<160> NUMBER OF SEQ ID NOS: 17

<210> SEQ ID NO 1
<211> LENGTH: 50
<212> TYPE: PRT
<213> ORGANISM: Homo sapiens

<400> SEQUENCE: 1

Asn Leu Lys Lys Ile Thr Arg Glu Gln Arg Arg His Met Lys Arg Trp
1               5                   10                  15

Glu Tyr Phe Ile Ala Ala Glu Glu Val Ile Trp Asp Tyr Ala Pro Val
            20                  25                  30

Ile Pro Ala Asn Met Asp Lys Lys Tyr Arg Ser Gln His Leu Asp Asn
        35                  40                  45

Phe Ser
    50

<210> SEQ ID NO 2
<211> LENGTH: 42
<212> TYPE: PRT
<213> ORGANISM: Homo sapiens

<400> SEQUENCE: 2

Asn Leu Lys Lys Ile Thr Arg Glu Gln Arg Arg His Met Lys Arg Trp
1               5                   10                  15
```

Glu Tyr Phe Ile Ala Ala Glu Glu Val Ile Trp Asp Tyr Ala Pro Val
            20                  25                  30

Ile Pro Ala Asn Met Asp Lys Lys Tyr Arg
        35                  40

<210> SEQ ID NO 3
<211> LENGTH: 10
<212> TYPE: PRT
<213> ORGANISM: Homo sapiens

<400> SEQUENCE: 3

Asn Leu Lys Lys Ile Thr Arg Glu Gln Arg
1               5                   10

<210> SEQ ID NO 4
<211> LENGTH: 10
<212> TYPE: PRT
<213> ORGANISM: Homo sapiens

<400> SEQUENCE: 4

Thr Arg Glu Gln Arg Arg His Met Lys Arg
1               5                   10

<210> SEQ ID NO 5
<211> LENGTH: 10
<212> TYPE: PRT
<213> ORGANISM: Homo sapiens

<400> SEQUENCE: 5

Arg His Met Lys Arg Trp Glu Tyr Phe Ile
1               5                   10

<210> SEQ ID NO 6
<211> LENGTH: 10
<212> TYPE: PRT
<213> ORGANISM: Homo sapiens

<400> SEQUENCE: 6

Trp Glu Tyr Phe Ile Ala Ala Glu Glu Val
1               5                   10

<210> SEQ ID NO 7
<211> LENGTH: 10
<212> TYPE: PRT
<213> ORGANISM: Homo sapiens

<400> SEQUENCE: 7

Ala Ala Glu Glu Val Ile Trp Asp Tyr Ala
1               5                   10

<210> SEQ ID NO 8
<211> LENGTH: 10
<212> TYPE: PRT
<213> ORGANISM: Homo sapiens

<400> SEQUENCE: 8

Ile Trp Asp Tyr Ala Pro Val Ile Pro Ala
1               5                   10

<210> SEQ ID NO 9
<211> LENGTH: 10
<212> TYPE: PRT
<213> ORGANISM: Homo sapiens

```
<400> SEQUENCE: 9

Pro Val Ile Pro Ala Asn Met Asp Lys Lys
1               5                   10

<210> SEQ ID NO 11
<211> LENGTH: 10
<212> TYPE: PRT
<213> ORGANISM: Homo sapiens

<400> SEQUENCE: 10

Asn Met Asp Lys Lys Tyr Arg Ser Gln His
1               5                   10

<210> SEQ ID NO 11
<211> LENGTH: 10
<212> TYPE: PRT
<213> ORGANISM: Homo sapiens

<400> SEQUENCE: 11

Tyr Arg Ser Gln His Leu Asp Asn Phe Ser
1               5                   10

<210> SEQ ID NO 12
<211> LENGTH: 5
<212> TYPE: PRT
<213> ORGANISM: Homo sapiens

<400> SEQUENCE: 12

Leu Asp Asn Phe Ser
1               5

<210> SEQ ID NO 13
<211> LENGTH: 5
<212> TYPE: PRT
<213> ORGANISM: Homo sapiens

<400> SEQUENCE: 13

Glu Tyr Phe Ala Glu
1               5

<210> SEQ ID NO 14
<211> LENGTH: 15
<212> TYPE: PRT
<213> ORGANISM: Homo sapiens

<400> SEQUENCE: 14

Pro Ile Ile Pro Ala Asn Met Asp Lys Lys Tyr Arg Ser Leu His
1               5                   10                  15

<210> SEQ ID NO 15
<211> LENGTH: 15
<212> TYPE: PRT
<213> ORGANISM: Homo sapiens

<400> SEQUENCE: 15

Ile Thr Arg Glu Gln Arg Arg His Met Lys Arg Trp Glu Tyr Phe
1               5                   10                  15

<210> SEQ ID NO 16
<211> LENGTH: 15
<212> TYPE: PRT
<213> ORGANISM: Homo sapiens

<400> SEQUENCE: 16
```

-continued

```
Arg Trp Glu Tyr Phe Ile Ala Ala Glu Glu Val Ile Trp Asp Tyr
1               5                   10                  15

<210> SEQ ID NO 17
<211> LENGTH: 13
<212> TYPE: PRT
<213> ORGANISM: Homo sapiens

<400> SEQUENCE: 17

Asp Ala Asp Ser Asp Tyr Gln Asp Glu Leu Ala Leu Ile
1               5                   10
```

THROMBIN GENERATION INHIBITORS

CROSS-REFERENCE TO RELATED APPLICATIONS

This application is a divisional of the commonly assigned, U.S. patent application Ser. No. 09/911,129, filed on Jul. 23, 2001, now U.S. Pat. No. 6,703,364, issued on Mar. 9, 2004.

This invention is supported, at least in part, by Grant No. R37 HL34575 from the National Institute of Health, USA. The U.S. government has certain rights in this invention.

FIELD OF THE INVENTION

The invention relates to methods and medicines for inhibiting blood coagulation.

BACKGROUND

Blood Coagulation

Blood coagulation is a process whereby blood thickens and gradually becomes a clot. The process is vitally important to the stoppage of bleeding when blood vessels are damaged. Blood coagulation occurs through a complex series of molecular reactions, ultimately resulting in conversion of soluble fibrinogen molecules, present in the blood, into insoluble threads of fibrin. The result is a blood clot which consists of a plug of platelets enmeshed in the insoluble fibrin network.

During the blood coagulation process, a cascade of proteins in the blood, called "clotting factors," are activated and catalyze the chemical reactions that result in a blood clot. These clotting factors comprise two convergent reaction pathways, initiated by different stimuli, both leading to clot formation. Clot formation in response to blood vessel damage results from activation of the extrinsic pathway. See FIG. 1. This pathway is initiated by display of tissue factor ("TF") protein on the surface of damaged blood vessels. Exposed TF binds to circulating factor VIIa to form an active protease that cleaves factor X to active factor Xa.

Blood clot formation in response to abnormalities in the blood vessel wall, in the absence of tissue injury, results from activation of the intrinsic pathway. See FIG. 1. This pathway is initiated by factor XII when contact is made between blood and exposed endothelial cell surfaces. This pathway, in a sequential reaction cascade involving factors XI, IX and VIII, and the active "a" forms of each of these factors, results in formation of factor Xa from factor X.

The formation of factor Xa from factor X is the point at which the extrinsic and intrinsic pathways converge. See FIG. 1. The resulting factor Xa then binds factor Va to form prothrombinase. Prothrombinase is a protease that cleaves prothrombin (also called "factor II") to yield thrombin (also called "α-thrombin" or "factor IIa"). α-Thrombin cleaves fibrinogen to form soluble fibrin monomers. α-Thrombin also cleaves factor XIII to active factor XIIIa. Factor XIIIa causes formation of covalent bonds between the soluble fibrin monomers, converting them into an insoluble fibrin polymer meshwork which, when combined with platelets, is the clot.

Inhibition and Reversal of Blood Coagulation

The blood coagulation process described above is regulated by an opposing group of factors, called anticoagulants, that inhibit coagulation or blood clotting. For example, formation of the TF/factor VIIa complex essential for progression of the extrinsic pathway, is inhibited by a protein called tissue factor pathway inhibitor ("TFPI"). See FIG. 1. Factors Va (interacts with factor Xa) and VIIIa (intrinsic pathway) are inhibited by anticoagulant-activated protein C ("APC") and its associated cofactor, protein S. Production of APC is activated by α-thrombin after binding to thrombomodulin. Finally, antithrombin III ("ATIII") functions by inactivating factor Xa and thrombin.

At any given time in the blood, the overall balance of blood coagulants and blood anticoagulants determines whether blood will clot. Normally, the balance is in favor of the anticoagulants and the blood circulates freely throughout the body. However, in response to injury or trauma, the coagulants increase in concentration and cause clotting of the blood.

In addition to physiologic inhibitors of blood coagulation, the body possesses a system to actively remove clots that have already formed. Circulating blood contains plasminogen, which binds to the fibrin molecules comprising a blood clot. Nearby cells release an inactive form of tissue plasminogen activator ("TPA") which binds to fibrin, is subsequently activated, then cleaves plasminogen to plasmin. Plasmin digests fibrin and dissolves the clot.

There exist human disorders, called "thromboses," where blood clots when it normally should not. Thrombosis is a major cause of death due to occlusion of arteries, which leads to heart attacks, strokes and peripheral ischemia (i.e., local deficiencies in blood supply). Thrombosis can also cause occlusion of venous blood vessels and result in pulmonary emboli.

In order to prevent or treat such thrombotic disorders, therapeutic methods to inhibit clot formation or to dissolve clots have been developed. Existing anticoagulants (that inhibit blood clot formation), for example, include heparin, which greatly increases activity of the physiologic anticoagulant, ATIII, in the blood. Warfarins are anticoagulants that are vitamin K antagonists. Since vitamin K is required for synthesis or functioning of a number of clotting factors (i.e., factors II, VII, IX and X, as well as a-thrombin and proteins C and S), sequestration of vitamin K inhibits coagulation.

The existing blood anticoagulants, however, produce side effects. For example, heparin administration can cause bleeding and thrombocytopenia (i.e., decrease in platelets). A disadvantage of warfarins is that it takes several days for their maximum effect to be realized. As with heparin, bleeding can also be a complication. Warfarins are also teratogens and can cross the placenta, causing fetal abnormalities when administered to pregnant women.

Thrombolytic agents, which dissolve existing clots, are also used therapeutically. Their activity is based on enhancing the generation of plasmin from its plasminogen precursor. Such agents include recombinant TPA and streptokinase. Disadvantages of these thrombolytics include a systemic fibrinolytic activity that can result in bleeding throughout the body. Some thrombolytics (i.e., streptokinase) are also highly antigenic and can cause allergic reactions.

Therefore, there are problematic side effects with existing anticoagulant and thrombolytic drugs. An ideal drug that prevents blood clot formation would target single clotting factors such that side effects resulting from nonspecific action of the drug are eliminated. Such ideal drugs would have superior efficacy and safety profiles since thromboses would be inhibited without bleeding as a side effect. Additionally, because of the many different manifestations and etiologies of thrombosis, and the different locations in the body where clots can form, there is a need for new and varied treatments for these manifestations.

SUMMARY OF THE INVENTION

In accordance with the present invention, it has been discovered that certain peptides derived from the region comprising amino acids 307 to 356 of the human blood coagulation factor Va exhibit excellent blood anticoagulation properties with little or no adverse side effects.

Thus, the present invention provides, as a new composition of matter, a peptide which is from 3 to 50 amino acids in length which contains a sequence (a) of at least 3 amino acids which is identical to a sequence found within amino acids 307 to 356 of the human blood clotting factor Va (SEQ ID NO. 1), but excluding the peptide comprising amino acids 311 to 325 (SEQ ID NO. 15) and the peptide comprising amino acids 321 to 335 (SEQ ID NO. 16). The peptide can further contain additional amino acid sequences at the N-terminal end of sequence (a), the C-terminal end of sequence (a), or both the N- and C-terminal ends of sequence (a), as long as the amino acid sequence of the entire peptide is at least 60% identical to a sequence within SEQ ID NO. 1. The peptide further exhibits an $IC_{50}$ of between 50 nM to 500 µM for inhibition of prothrombinase In addition, the present invention also provides a pharmaceutical composition comprising one or more of the above inhibitory peptides and a pharmaceutically acceptable carrier.

The present invention also provides new processes for reducing and preventing unwanted clotting of blood in mammals, including humans, comprising administering these pharmaceutical compositions to the mammals.

BRIEF DESCRIPTION OF THE DRAWINGS

The present invention may be more readily understood by reference to the following drawings wherein:

FIG. 2 is a diagram of amino acid sequences of the peptides contained in the 307 to 356 region of human blood coagulation factor Va;

DETAILED DESCRIPTION OF THE INVENTION

Definitions

Figure 1:
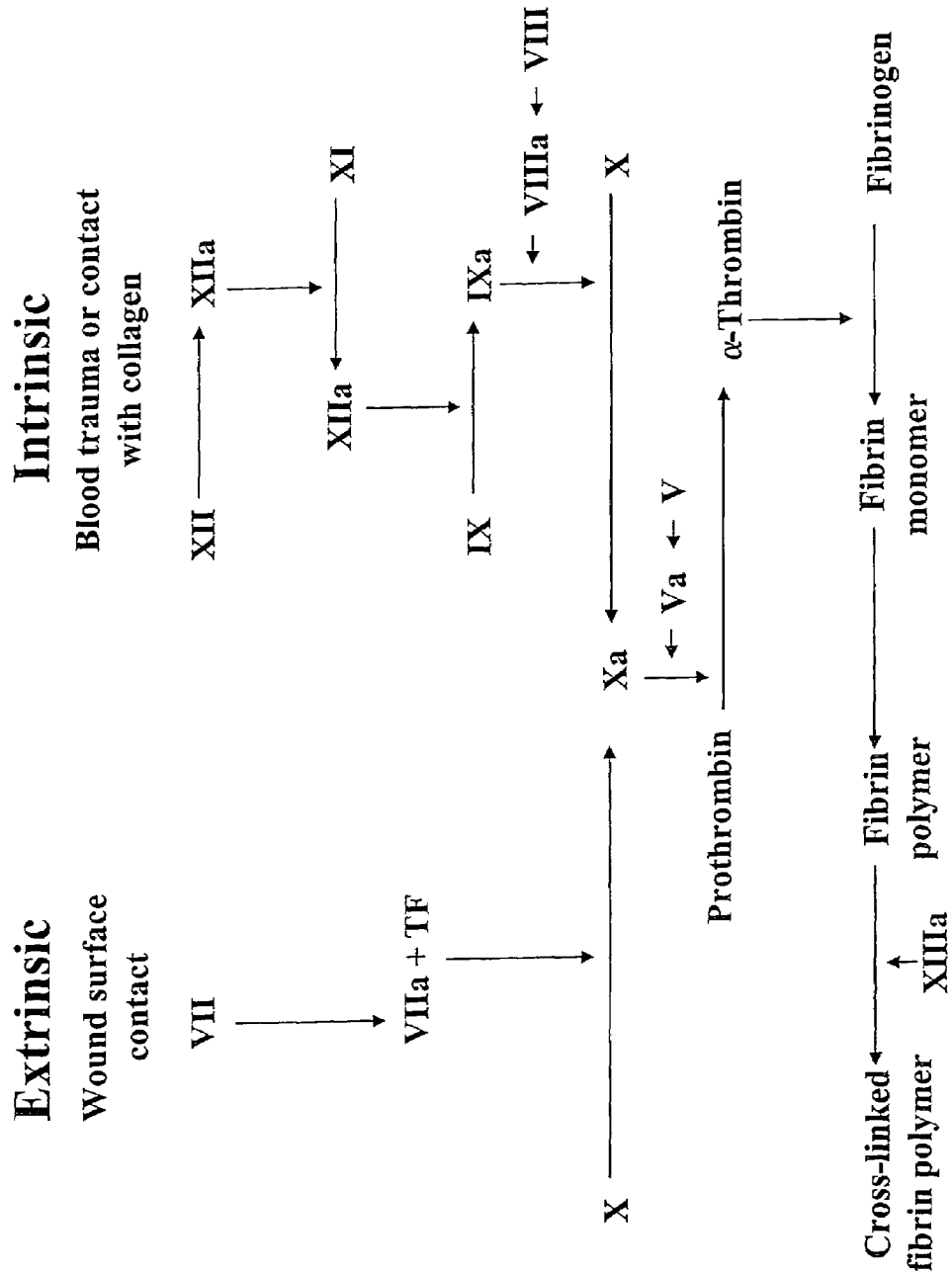
FIG. 1 is a schematic diagram illustrating the blood coagulation pathways in humans.

Unless otherwise indicated, the following terms used in this document have the following meanings:

"Amino acid" refers to a carboxylic acid having an amino group attached to the α carbon atom. Such amino acids are naturally occurring L amino acids, unless otherwise specifically indicated. The commonly used one- and three-letter abbreviations for amino acids are use herein (Lehninger, 1975, in *Biochemistry*, 2nd edition, Worth Publishers, New York, pp. 71–92).

"Peptide bond" refers to the chemical bond formed between the α-amino group of one amino acid and the α-carboxyl group of a second amino acid (i.e., amide linkages).

"Protein" describes a linear polymer or sequence of amino acids, joined by peptide bonds. Such proteins are naturally occurring, meaning that they can be isolated from cells or tissues.

"Peptide" also refers to a linear polymer or sequence of amino acids, joined by peptide bonds. Peptides, however, are not naturally occurring in that they cannot be isolated from cells or tissues. Instead, peptides can be obtained from chemical synthesis in which peptide bonds are formed between amino acids, and between amino acids and peptides. Herein, peptides can be from 3 amino acids long to about 50 amino acids long.

Proteins and peptides are defined by a linear sequence of amino acids. An amino acid sequence has a free amino group at the N-terminal end and a free carboxyl group at the C-terminal end. In the notation used herein to describe the amino acid sequence of a protein or peptide, the lefthand end of an amino acid sequence denotes the N-terminal end, and the righthand end denotes the C-terminal end.

"Inhibition of prothrombinase activity" refers to the ability of peptides to inhibit blood coagulation by inhibition of prothrombinase activity. The peptides interfere with the ability of factor Va to associate with factor Xa to form a functional prothrombinase enzyme.

"Modified peptides" refers to peptides that have one or more of the following: i) one or more amino acids that are non-naturally occurring, ii) one or more D-amino acids, and iii) one or more non-hydrolyzable bonds between adjacent amino acids. Additionally, modified peptides include cyclized peptides.

"Medicines" refer to substances administered to mammals, including humans, to prevent or treat a disease.

"Carrier" refers to an organic or inorganic ingredient, natural or synthetic, with which the peptides can be combined to facilitate administration.

"Pharmaceutically-acceptable carrier" refers to one or more compatible solid or liquid filler, diluents or encapsulating substances which are suitable for administration into a human or other animal. The components comprising these carriers are capable of being commingled with the peptides, and with each other, in a manner such that there is no interaction which would substantially impair the desired pharmaceutical efficacy.

Factor Va and the Prothrombinase Complex

In accordance with the present invention, it has been found that certain peptides derived from amino acids 307 to 357 of the human blood coagulation factor Va exhibit excellent anticoagulation properties with little or no adverse side effects.

The point at which the intrinsic and extrinsic blood coagulation pathways converge is an ideal point for an anticoagulant molecule to act since inhibition at this point blocks both pathways. See FIG. 1. Additionally, at the point where the intrinsic and extrinsic pathways converge, the prothrombinase complex is formed. Prothrombinase cleaves prothrombin to form α-thrombin, a central step in blood coagulation. See FIG. 1. Inhibition of this step in the coagulation pathway, through inhibition of prothrombinase in accordance with the present invention, is an efficient way of blocking blood coagulation.

Prothrombinase is an enzyme comprised of two subunits. The first subunit, factor Xa, can itself cleave α-thrombin and, therefore, is the enzymatic subunit of prothrombinase. The second subunit, factor Va, cannot by itself cleave α-thrombin, but increases the cleavage activity of factor Xa 300,000 times. Factor Va, therefore, is called the non-enzymatic subunit of prothrombinase. The prothrombinase enzyme (factor Xa plus factor Va) associates with its substrate, prothrombin, on a cell membrane surface, in the presence of $Ca^{2+}$. See FIG. 1.

The factor Va subunit of prothrombinase is itself comprised of two subunits, both derived from a circulating protein called factor V. In the blood, α-thrombin cleaves factor V to produce the two factor Va subunits. The first subunit, called the heavy chain, comprises amino acids 1–713 of factor V and has a molecular weight of 94,000 daltons. The second subunit, called the light chain, comprises amino acids 1537–2183 of factor V and has a molecular weight of 74,000 daltons. The heavy and light chain subunits associate non-covalently, through divalent metal ions, to form factor Va. Factor Va associates with factor Xa and prothrombin to form prothrombinase.

The peptides which provide enhanced anticoagulation activity in accordance with the present invention are peptides from a 50 amino acid region (SEQ ID NO. 1) of the 713 amino acid factor Va heavy chain. The peptides can be further described as those peptides having no more than 50 total amino acids and which further include an amino acid sequence (a) of at least 3 amino acid units long which is identical to an amino acid sequence contained in the human blood clotting factor Va comprising amino acid 307 through amino acid 356 (SEQ ID NO. 1) of factor Va. Preferred peptides have (a) amino acid segments of 5, 7, 10 or 12 amino acids long which are identical to those in the 307 to 356 region of factor Va. Preferably, the (a) amino acid segments that are identical to those in factor Va come from two particular regions within the region encompassing amino acids 307 to 356 of factor Va. The first preferred region from which the (a) amino acid segments are derived includes amino acids 317 to 341 of factor Va. The second preferred region from which the (a) amino acid segments are derived include amino acids 347 to 356 of factor Va. The 317 to 341 and 347 to 356 regions of factor Va are shown in FIG. 2 as the underlined amino acid sequences within SEQ ID NO. 1.

The (a) amino acid segments of each inventive peptide can optionally contain additional amino acid sequences. One such additional sequence may be added to the N-terminal end of the (a) segment. Another such additional sequence may be added to the C-terminal end of the (a) segment. Amino acid sequences can be present on both the N- and C-terminal ends of the (a) segment. Such additions can be made as long as the resulting peptide is no longer than 50 amino acids in length and the amino acid sequence of the entire peptide is at least 60% identical to a sequence within SEQ ID NO. 1.

Percent identity of an inventive peptide to a sequence within SEQ ID NO. 1 is determined by aligning the (a) amino acid sequence of the inventive peptide with the identical amino acids contained within the amino acid sequence 307 through 356 of factor Va (SEQ ID NO. 1). If the inventive peptide has additional amino acid sequences present on either the N-terminal, the C-terminal, or the N- and C-terminal ends of the (a) segment, each amino acid in such additional sequence(s) is compared with the amino acid within SEQ ID NO. 1 with which it is aligned. That is, after the (a) segment of the inventive peptide is aligned with the identical amino acids contained within SEQ ID NO. 1, the additional sequences, if any, present at the N-terminal, C-terminal, or N- and C-terminal ends of segment (a) will be aligned with amino acids within SEQ ID NO. 1 at the same position. These amino acids are compared to one another. The result of such comparison is that each amino acid within the inventive peptide is either identical to the amino acid at the same position within SEQ ID NO. 1, or it is not identical. After such identity or non-identity is determined for each amino acid within the inventive peptide, the percent identity of the entire inventive peptide to SEQ ID NO. 1 is determined by dividing the number of amino acids within the inventive peptide that are identical to amino acids at the same position within SEQ ID NO. 1 by the total number of amino acids within the inventive peptide. This number is then multiplied by 100 to give the percent identity of the inventive peptide to SEQ ID NO. 1 ([no. of identical amino acids/total number of amino acids]×100). By definition, since the (a) segment of an inventive peptide is identical to an amino acid sequence contained within amino acids 307 through amino acid 356 of factor Va (SEQ ID NO. 1), the (a) peptide has 100% identity to a sequence within SEQ ID NO. 1. Inventive peptides that have additional amino acid sequences present at the N-terminal, C-terminal, or N- and C-terminal ends of segment (a) will have an identity to SEQ ID NO. 1 that is less than 100%.

The inventive peptides preferably provide an $IC_{50}$ of between 50 nM to 500 μM, more preferably 50 nM to 250 μM, most preferably 50 nM to 150 μM, for inhibition of prothrombinase with little or no adverse side effects.

Examples of particular peptide segments of the present invention are illustrated in FIG. 2. The first row in this figure illustrates the amino acid sequence of human blood clotting protein factor Va, ranging from amino acids 307–356, inclusive (SEQ ID NO. 1). In the column at the left in the figure, the name of each peptide is given. To the right of each name designation, the amino acid sequence of each peptide of the present invention is given. In the column at the right in the figure, the SEQ ID NO. of each peptide is given. The amino acid sequence of each individual peptide is vertically aligned underneath the region of the 307–356 sequence (first row) from which it was derived.

As shown in FIG. 2, one peptide segment of the present invention, which is identified as NR42 (SEQ ID NO. 2), is a 42 amino acid peptide encompassing amino acids 307–348 of the human factor Va heavy chain. Other peptides of the present invention, which are identified as AP1–AP9 (SEQ ID NO. 3–11), comprise a series of overlapping, 10 amino acid peptides that span the region 307–356 of human factor Va. Still other peptides of the present invention are L5S (SEQ ID NO. 12), a 5 amino acid peptide encompassing amino acids 352–356 of human factor Va. Still another is P15H (SEQ ID NO. 14), which is a 15 amino acid peptide encompassing amino acids 337–351 of human factor Va.

Another peptide of the present invention is the tripeptide EYF, that encompasses amino acids 323–325 of the factor Va heavy chain. See FIG. 2. The particular inventive peptide is EYFAE (SEQ ID NO. 13). The EYFAE peptide contains the EYF amino acid sequence that is identical to the amino acid sequence located at 323–325 of SEQ ID NO. 1. The EYF amino acid sequence of the EYFAE inventive peptide represents the (a) amino acid sequence of this peptide. The EYFAE peptide contains two additional amino acids, AE, added to the C-terminal end of the EYF sequence. When the EYF amino acid sequence of the EYFAE inventive peptide is aligned with the identical EYF amino acid sequence, located at 323–325 of SEQ ID NO. 1, the AE sequence of the inventive peptide is aligned with the amino acid sequence IA, located at 326–327 of SEQ ID NO. 1. The A at position 326 of the inventive peptide is not identical to the I at the same position of SEQ ID NO. 1. Likewise, the E at position 327 of the inventive peptide is not identical to the A at the same position of SEQ ID NO. 1. Therefore, out of a total of 5 amino acids that comprise the EYFAE inventive peptide, 3 amino acids (i.e., EYF) are identical to amino acids at the same position of SEQ ID NO. 1. Using these numbers, percent identity of the EYFAE inventive peptide to SEQ ID NO. 1 is 60% ([3/5]×100).

Two peptide sequences within the region between amino acids 307 and 356 of the human factor Va protein, namely VP311 encompassing amino acids 311 to 325 (SEQ ID NO. 15) and VP321 encompassing amino acids 321 to 335 (SEQ ID NO. 16) have already been disclosed in the literature. See Kojima, et al., 1998, J Biol Chem, 273:14900–5. Accordingly, they are not new peptides provided by the present invention.

Inhibition of Prothrombinase by the Peptides

As indicated above, the present invention is based on the recognition that the inventive peptides exhibit excellent anticoagulation activity, in particular for inhibition of prothrombinase, and preferably provide an $IC_{50}$ of between 50 nM to 500 µM, more preferably between 50 nM to 250 µM, most preferably between 50 nM to 150 µM, for the inhibition of prothrombinase. This can be more easily understood by reference to FIGS. 3, 4, 5 and 6.

Figure 3:
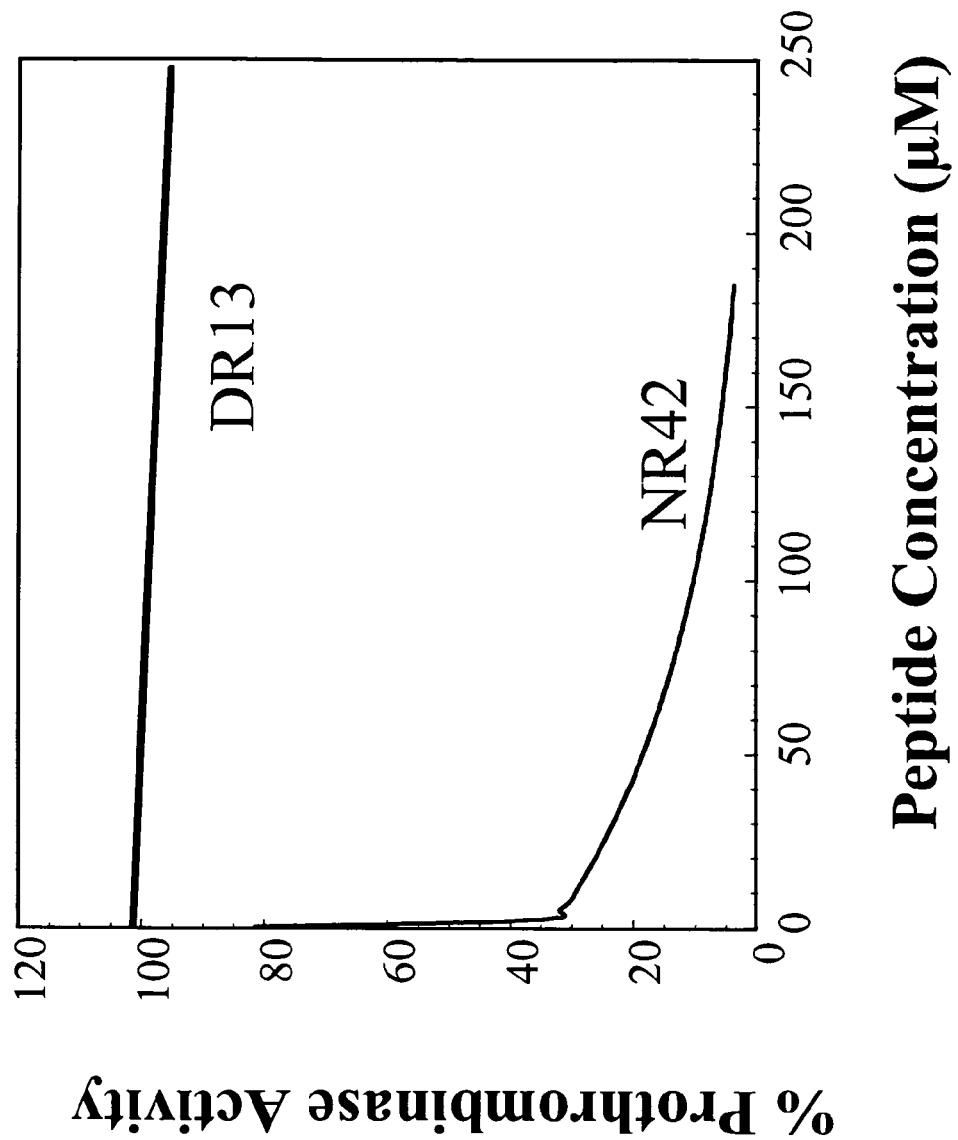
FIG. 3 is a graph showing inhibition of prothrombinase activity by one of the peptides (SEQ ID NO. 2)

FIG. 3 is a graph showing inhibition of prothrombinase activity by the 42 amino acid peptide NR42, encompassing amino acids 307–348 of the human factor Va heavy chain (SEQ ID NO. 2). The assay used to obtain the data shown in FIG. 3 is a visual blood clotting assay that is described in detail in Example 2 of this document.

Briefly, in the visual blood clotting assay, reactions are set up that contain all components of the blood necessary to form a blood clot and the time required for formation of a visual blood clot is recorded. To test inhibitory activity of the NR42 peptide, different concentrations of NR42 are added to a series of such reactions. The x-axis of FIG. 3, labeled "Peptide Concentration," shows the range of NR42 peptide concentrations tested. The time required for an observable blood clot to form in the absence of NR42 peptide (0 µM peptide on the x-axis) is designated as 100% prothrombinase activity, as shown on the y-axis of FIG. 3. Inhibition of blood clotting by NR24 results in longer clotting times. Longer clotting times are shown on the y-axis of the graph as decreased prothrombinase activity. For example, a clotting time in the presence of peptide that is twice as long as the clotting time in the absence of peptide is represented as 50% prothrombinase activity on the graph.

The data in FIG. 3 show that, as increasing concentrations of NR42 peptide are added to the clotting reactions, prothrombinase activity decreases, reflecting the ability of the NR42 peptide to inhibit blood coagulation. See the line labeled "NR42" in the FIG. 3 graph.

The concentration of peptide at which factor Va activity is 50% of the activity in the absence of peptide is called the $IC_{50}$. Using a given set of reaction conditions, $IC_{50}$ values can be used to compare the ability of different peptides to inhibit blood clotting. Lower values for $IC_{50}$ indicate a better inhibitor of prothrombinase activity. $IC_{50}$ for the NR42 peptide is approximately 1.3 µM, as determined using the visual blood clotting assay (using the fluorescent prothrombinase assay, described below, the $IC_{50}$ is determined to be approximately 0.5 µM).

In contrast to the inhibitory activity of NR42, increasing concentrations of a control peptide, DR13, encompassing amino acids 697 to 709 of the factor Va heavy chain (SEQ ID NO 17; see FIG. 2), do not significantly affect blood clotting time and prothrombinase activity. (See the line labeled "DR13" in the FIG. 3 graph.)

Figure 4:
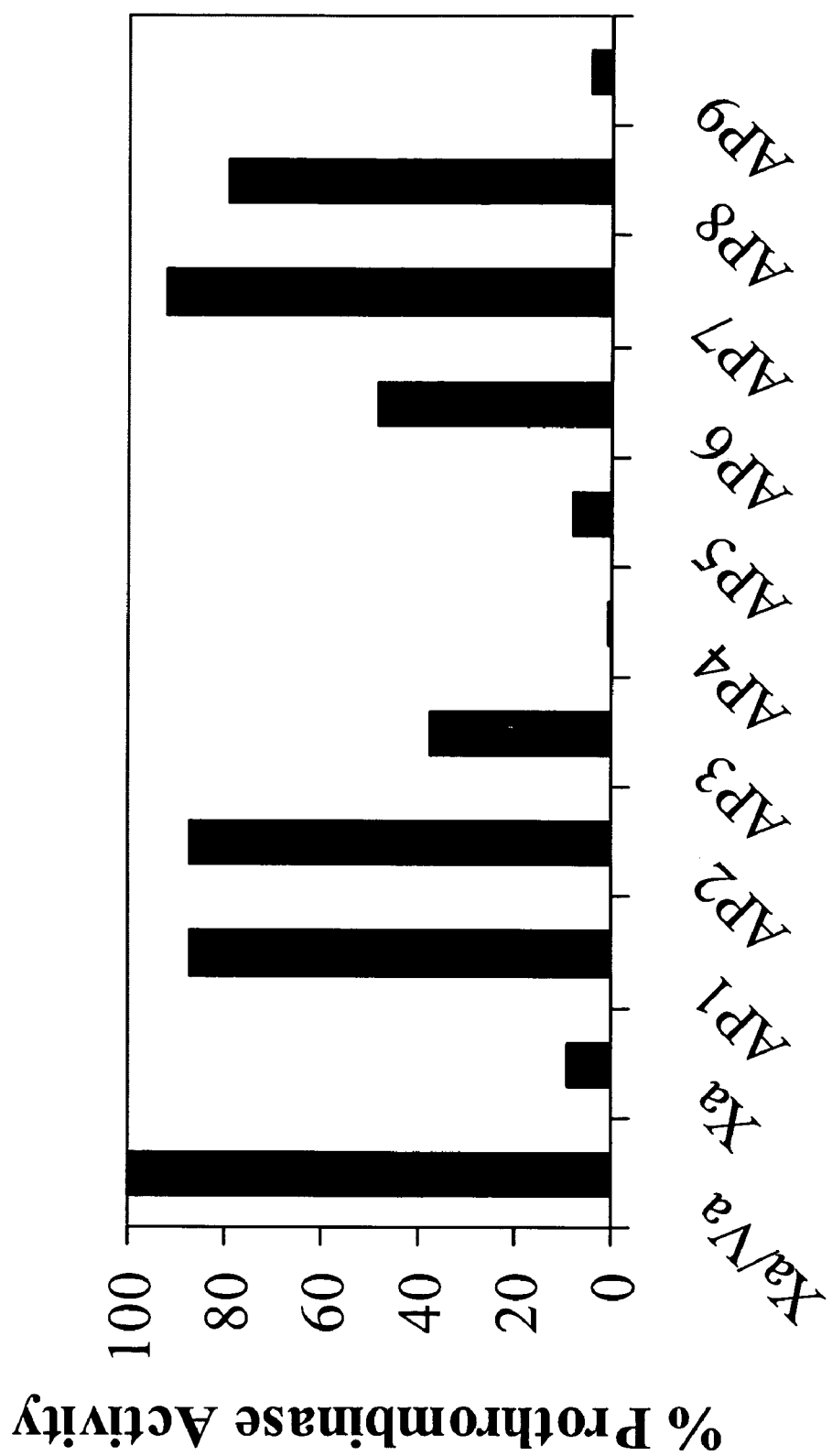
FIG. 4 is a graph showing inhibition of prothrombinase activity by 100 µM of nine different peptides (SEQ ID NOS. 3–11)

FIG. 4 is a bar graph showing inhibition of prothrombinase activity by a series of shorter peptides, each 10 amino acids in length, that span amino acids 307 to 356 of the human factor Va heavy chain. These peptides, designated AP1 through AP9 (SEQ ID NO. 3 through SEQ ID NO. 11) are shown in FIG. 2.

The assay used to obtain the data shown in FIG. 4 is a fluorescent assay that is described in Example 3 of this document. Briefly, the fluorescent assay, in contrast to the visual assay, measures only one reaction of the many necessary for formation of a blood clot. The fluorescent assay measures conversion of prothrombin to α-thrombin as catalyzed by prothrombinase. See FIG. 1. A fluorescent assay reaction contains prothrombin, factor Xa, factor Va and a preparation of phospholipid vesicles, which facilitate assembly of the aforementioned components into a functioning prothrombinase enzyme.

Each fluorescent assay also contains a fluorescent compound called dansylarginine-N-(3-ethyl-1,5-pentanediyl) amide (or DAPA for short). DAPA specifically binds to α-thrombin, the product of the prothrombinase reaction. Binding of DAPA by α-thrombin increases the fluorescence intensity of DAPA. In the case where no peptide inhibitor of prothrombinase is present in the reaction, high levels of α-thrombin are produced in the reaction, and DAPA fluorescence is high. When a peptide inhibitor of prothrombinase is present, little α-thrombin is produced in the reaction, and DAPA fluorescence is low. Therefore, by measuring DAPA fluorescence, the inhibitory ability of each peptide is determined.

FIG. 4 shows a bar graph where each bar represents a prothrombinase reaction containing DAPA, as described above, and 100 µM of peptides AP1 through AP9. The identity of reactions containing each peptide, as well as the reactions containing no peptide (labeled "Xa/Va") or no peptide and no factor Va (labeled "Xa") is shown on the x-axis of FIG. 4.

Activities of prothrombinase, as measured by DAPA fluorescence, are shown on the y-axis of FIG. 4. Prothrombinase activity in the absence of peptide (the bar labeled "APXa/Va" in FIG. 4) is designated as 100%. DAPA fluorescence in the absence of both peptide and factor Va (the bar labeled "APXa" in FIG. 4) is 9% of the APXa/Va activity, and is background fluorescence.

As shown in FIG. 4, 100 µM of AP4 peptide (SEQ ID NO. 6) results in less than 1% the prothrombinase activity of the reaction containing no peptide. Likewise, AP9 (SEQ ID NO. 11) has about 5%, and AP5 (SEQ ID NO. 7) about 8% the prothrombinase activity of the no peptide reaction. In addition, AP3 (SEQ ID NO. 5) has about 38% and AP6 (SEQ ID NO. 8) about 48% the prothrombinase activity of the no peptide reaction.

As shown in FIG. 2, the inventive peptides that inhibit prothrombinase activity (i.e., AP3, AP4, AP5, AP6 and AP9) comprise two distinct regions of amino acids 307 to 356 of factor Va (SEQ ID NO. 1). The first region comprises amino acids 317 to 341 of SEQ ID NO. 1. The second region comprises amino acids 347 to 356 of SEQ ID NO. 1. These two regions are shown in FIG. 2 as the underlined amino acid sequences within SEQ ID NO. 1.

In separate studies, the $IC_{50}$ values for some of these peptides is measured. $IC_{50}$ for AP4 (SEQ ID NO. 6) is approximately 5 μM. $IC_{50}$ for AP6 (SEQ ID NO. 8) is approximately 30 μM.

Figure 5:
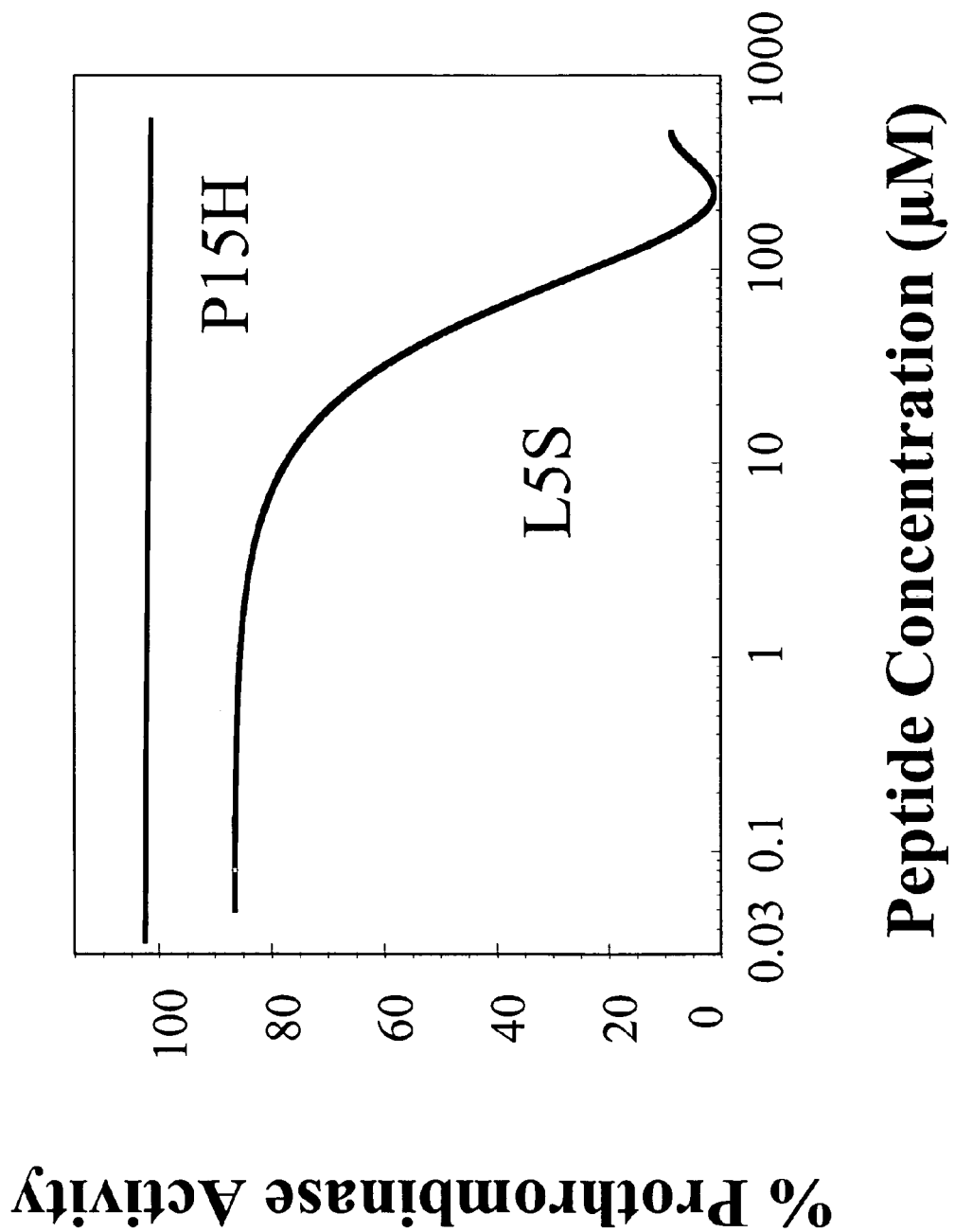
FIG. 5 is a graph showing inhibition of prothrombinase activity by one of the peptides (SEQ ID NO. 12)

FIG. 5 is a graph showing inhibition of prothrombinase activity by a 5 amino acid peptide, L5S, encompassing amino acids 352–356 of the human factor Va heavy chain (SEQ ID NO. 12). The assay used to obtain these data is the fluorescent assay that measures conversion of prothrombin to α-thrombin, as described above. In this study, a series of reactions is set up, each containing a different concentration of L5S, as shown on the x-axis of FIG. 5. Percent prothrombinase activity is obtained after measurement of DAPA fluorescence in the reactions containing the L5S peptide and comparison to an identical reaction containing no peptide, as described above. Prothrombinase activity in the absence of L5S is designated as 100% activity. Decreased activity, due to L5S inhibition, is designated as less than 100%.

The data in FIG. 5 show that the L5S peptide inhibits prothrombinase activity. From the figure, the concentration of L5S at which prothrombinase activity is 50% of the value without inhibitor (the $IC_{50}$) is approximately 50 μM. As shown in FIG. 2, the L5S inventive peptide comes from one of the two regions within SEQ ID NO. 1 that have prothrombinase inhibitory activity. The particular region of SEQ ID NO. 1 from which the L5S peptide comes comprises amino acids 347 to 356 of SEQ ID NO. 1.

As a control, a separate set of reactions is set up using a 15 amino acid peptide, P15H, encompassing amino acids 337–356 of factor Va (SEQ ID NO. 14). FIG. 5 shows that this peptide does not inhibit prothrombinase activity.

Figure 6:
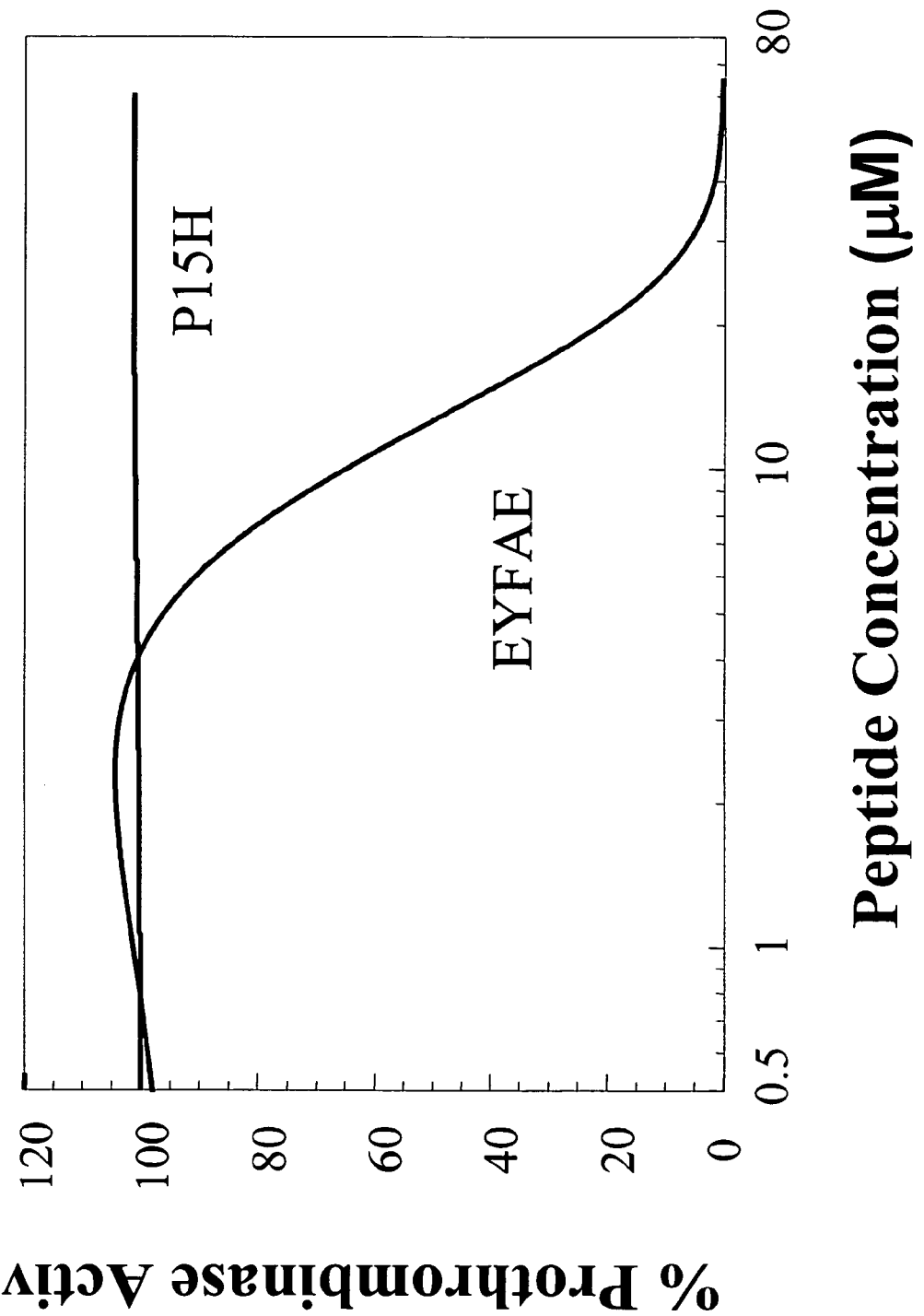
FIG. 6 is a graph showing inhibition of prothrombinase activity by another of the peptides (SEQ ID NO. 13).

FIG. 6 is a graph showing inhibition of prothrombinase activity by a 5 amino acid peptide, EYFAE (SEQ ID NO. 13). EYFAE encompasses amino acids 323 to 325 of the human factor Va heavy chain (i.e., EYF) and additionally includes the amino acids AE attached to the C-terminal end of the peptide. The assay used to obtain the data in FIG. 6 is the fluorescent assay that measures conversion of prothrombin to α-thrombin, as described above. The concentration of EYFAE peptide used in each reaction is shown on the x-axis of FIG. 6. The data in FIG. 6 show that the EYFAE peptide inhibits prothrombinase activity. From the figure, the concentration of EYFAE at which prothrombinase activity is 50% of the value without inhibitor (the $IC_{50}$) is in the range of approximately 10–15 μM.

Modified Peptides

One modification that the inventive peptides may contain are amino acids that are non-naturally occurring. Naturally occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. Some examples of non-naturally occurring amino acids are norleucine, norvaline, alloisoleucine, homoarginine, thiaproline, dehydroproline, hydroxyproline, homoserine, cyclohexylglycine, -amino-n-butyric acid, cyclohexylalanine, aminophenylbutyric acid, phenylalanines substituted at the ortho, meta, or paraposition of the phenyl moiety with one or two of the following, a $(C_1-C_4)$ alkyl, $(C_1-C_4)$ alkoxy, halogen, or nitro groups or substituted with a methylenedioxy group, 2- and 3-thienylalanine, -2- and 3-furanylalanine, -2-, 3-, and 4-pyridylalanine, -(benzothienyl-2- and 3-yl)alanine, -(1- and 2-naphthyl)alanine, O-alkylated derivates of serine, threonine, or tyrosine, S-alkylated cysteine, the O-sulfate ester of tyrosine, 3,5-diiodotyrosine and the D-isomers of the naturally occurring amino acids. These and any other non-naturally occurring amino acids can be included in the inventive peptides so long as they do not adversely affect the anticoagulation activity of these peptides, or provide adverse side effects, in any significant way.

Another modification that may be embodied in the inventive peptides is that they may contain one or more D-amino acids, rather than the L-amino acids that are found in naturally-occurring proteins. L and D refer to the stereochemistry of the amino acids. More specifically, L and D refer to the absolute configuration of the four atoms attached to the α carbon atom of the amino acid. L and D are designations well known to those skilled in the art. Peptide bonds involving D amino acids are less susceptible to cleavage by proteases than are peptide bonds involving L amino acids. Peptides containing D amino acids, therefore, may have a longer half life in vivo than peptides that do not contain D amino acids.

Also embodied in the present invention are peptides containing one or more non-hydrolyzable bonds between adjacent amino acids. Such non-hydrolyzable bonds are different than the aforementioned amide linkages between the α-amino group of one amino acid and the α-carboxyl group of a second amino acid (—CO—NH—). Such non-hydrolyzable bonds may include, for example, —CH$_2$NH—, —CH$_2$S—, —CH$_2$O—, —CH$_2$CH$_2$—, —CH=CH—(cis and trans), —COCH$_2$—, —CH(OH)CH$_2$—, —CH$_2$SO—, —CH$_2$SO$_2$—, and —CH(CN)NH—. These bonds can be formed by methods known in the art. The following references describe preparation of peptide analogs which include these alternative-linking moieties: Spatola, March 1983, "Peptide Backbone Modifications" (general review) Vega Data, Vol. 1, Issue 3; Spatola, 1983, in *Chemistry and Biochemistry of Amino Acids, Peptides and Proteins* (general review), B. Weinstein editor, Marcel Dekker, New York, p. 267; Morley, 1980, Trends Pharm. Sci., 468:463–468 (general review); Hudson, et al., 1979, Int. J. Pept. Prot. Res. 14:177–185 (—CH$_2$NH—, —CH$_2$CH$_2$—); Spatola, et al., 1986, Life Sci. 38:1243–1249 (—CH$_2$S—); Hann, 1982, Chem. Soc. Perkin Trans. I, pp. 307–314 (—CH=CH—, cis and trans); Almquist, et al., 1980, J. Med. Chem. 23:1392–1398 (—COCH$_2$—); Jennings-White, et al., 1982, Tetrahedron Lett. 23:2533 (—COCH$_2$—); Szelke, et al., 1982, European Application EP 45665; CA:97:39405 (—CH(OH)CH$_2$—); Holladay, et al., 1983, Tetrahedron Lett 24:4401–4404 (—CH(OH)CH$_2$—); and Hruby, 1982, Life Sci. 31:189–199 (—CH$_2$S—).

Another modification that may be contained in the inventive peptides are modifications that result in peptides called "constrained peptides" (including cyclized peptides). One example of a cyclized peptide is a peptide that has at least one cysteine amino acid at or near each end of the peptide. Through formation of intramolecular disulfide bridges between the cysteines, the peptide becomes cyclized. Such constrained peptides may be generated by methods known in the art (Rizo and Gierasch, 1992, Annu Rev Biochem, 61:387–418) and are more resistant to proteases in vivo than are peptides of the same amino acid sequence that are not cyclized.

Methods of Synthesizing Peptides

A wide variety of different techniques are known for making peptide segments, and any such method can be used in making the inventive peptides.

Most often, synthesis of peptides involves chemical synthesis and can include subsequent treatment under oxidizing conditions appropriate to obtain the native conformation, that is, the correct disulfide bond linkages. This can be accomplished using methodologies well known to those skilled in the art (Kelly and Winkler, 1990, in *Genetic Engineering Principles and Methods*, vol. 12, J. K. Setlow editor, Plenum Press, New York, pp. 1–19; Stewart and Young, 1984, Solid Phase Peptide Synthesis, Pierce Chemical Co., Rockford, Ill.). One such method is described below.

In one embodiment, peptides of the invention can be prepared using solid phase synthesis (Merrifield, 1964, J Amer Chem Soc, 85:2149; Houghten, 1985, Proc Natl Acad Sci USA, 82:5131–5). Solid phase synthesis can begin at the C-terminus of the putative peptide by coupling a protected amino acid to a suitable resin. In this synthesis, the carboxyl terminal amino acid, with its α-amino group suitably protected, can be coupled to a chloromethylated polystyrene resin. After removal of the α-amino protecting group with, for example, trifluoroacetic acid (TFA) in methylene chloride and neutralizing in, for example TEA, the next cycle in the synthesis can proceed.

The remaining α-amino- and, if necessary, side-chain-protected amino acids can then be coupled sequentially in the desired order by condensation to obtain an intermediate compound connected to the resin. Alternatively, some amino acids may be coupled to one another forming a peptide prior to addition of the peptide to the growing solid phase peptide chain. The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, BOP [benzotriazole-1-yl-oxytris (dimethylamino) phosphonium hexafluorophosphate] method, N-hydroxysuccinic acid imido ester method, etc.), and Woodward reagent K method. In the case of elongating the peptide chain in the solid phase method, the peptide can be attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonyl-hydrazide resin can be used.

Common to chemical synthesis of peptides is the protection of the reactive side-chain R groups of the various amino acid moieties with suitable protecting groups at that site until the group is ultimately removed after the chain has been completely assembled. Also common is the protection of the a-amino group on an amino acid or a fragment while that entity reacts at the carboxyl group followed by the selective removal of the α-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the reactive amino side-chain groups of the various amino acid moieties are exemplified by benzyloxycarbonyl (abbreviated Z), isonicotinyloxycarbonyl (iNOC), O-chlorobenzyloxycarbonyl [Z(NO$_2$)], p-methoxybenzyloxycarbonyl [Z(OMe)], t-butoxycarbonyl, (Boc), t-amyioxycarbonyl (Aoc), isobornyloxycarbonyl, adamatyloxycarbonyl, 2-(4-biphenyl)-2-propyloxycarbonyl (Bpoc), 9-fluorenyl-methoxycarbonyl (Fmoc), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

As protective groups for carboxy groups there can be exemplified, for example, benzyl ester (OBzl), cyclohexyl ester (Chx), 4-nitrobenzyl ester (ONb), t-butyl ester (Obut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl ethylcarbamoyl, 4-methylbenzyl, 2,4,6-trimethy-benzyl (Tmb) etc, and the hydroxyl group in the serine can be protected with benzyl, t-butyl, acetyl, tetrahydropyranyl etc.

Stewart and Young, supra, provides detailed information regarding procedures for preparing peptides. Protection of a-amino groups is described on pages 14–18, and side-chain blockage is described on pages 18–28. A table of protecting groups for amine, hydroxyl and sulfhydryl functions is provided on pages 149–151.

After the desired amino acid sequence has been completed, the intermediate peptide can be removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence can be washed with ether, transferred to a large volume of dilute acetic acid, and stirred at pH adjusted to about 8.0 with ammonium hydroxide.

Preferably, in order to avoid alkylation of residues in the peptide, (for example, alkylation of methionine, cysteine, and tyrosine residues) a thio-cresol and cresol scavenger mixture can be used. The resin can be washed with ether, and immediately transferred to a large volume of dilute acetic acid to solubilize and minimize intermolecular cross-linking. A 250 µM peptide concentration can be diluted in about 2 liters of 0.1 M acetic acid solution. The solution can then be stirred and its pH adjusted to about 8.0 using ammonium hydroxide. Upon pH adjustment, the peptide takes its desired conformational arrangement.

Kunitz domains (i.e., functional sites) can be made either by chemical synthesis, described above, or by semisynthesis. The chemical synthesis or semisynthesis methods of making allow the possibility of modified amino acid residues to be incorporated. This has been carried out for Kunitz domains and related proteins as previously described (Beckmann, et al., 1988, Eur J Biochem, 176:675–82; Bigler, et al., 1993, Protein Sci, 2:786–99).

Use of Inventive Peptides as Medicines for Inhibiting Blood Coagulation

The peptides of the present invention can be used as medicines to prevent thrombotic disorders resulting from the formation of blood clots that obstruct blood vessels. There are a wide variety of conditions that predispose or lead to thrombosis. Some of these conditions are coronary artery disease, valvular heart disease, stable and unstable angina, myocardial infarction, atrial fibrillation and stroke. Other subjects at risk for thrombosis are those undergoing coronary angioplasty, those with coronary artery bypass grafts or prosthetic heart valves, those with high cholesterol levels in the blood, those that have catheters inserted into blood vessels, women taking oral contraceptives or individuals with genetic disorders causing a predisposition to blood coagulation.

When administered to a subject, the peptides of the invention can be given as pharmaceutically-acceptable compositions. Such compositions may routinely contain salt, buffering agents, preservatives, adjuvants, other vehicles and, optionally, other therapeutic agents. The peptides may be optionally combined with a pharmaceutically-acceptable carrier.

The peptides, generally speaking, may be administered using any mode that is medically acceptable, meaning any mode that produces effective levels of the active peptides without causing clinically unacceptable adverse effects. Such modes of administration include parenteral routes (e.g., intravenous, intra-arterial, subcutaneous, intramuscular, mucosal or infusion), but may also include oral, rectal, topical, nasal or intradermal routes. Other delivery systems can include time-release, delayed release or sustained release delivery systems. Such systems can avoid repeated administrations, increasing convenience to the subject and the physician. Many types of release delivery systems are available and known to those of ordinary skill in the art.

Compositions suitable for parenteral administration are preferred and conveniently comprise a sterile aqueous or oleaginous preparation of the peptide, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. The pharmaceutical compositions may conveniently be presented in unit dosage form and may be prepared by any of the methods well-known in the art of pharmacy.

The peptides of the present invention can be administered to humans in an amount that prevents formation of unwanted blood clots. Generally, such an amount will be from about 0.01 to 1000 mg/kg per day, more preferably from about 0.1 to 100 mg/kg per day, most preferably from about 1 to 10 mg/kg per day. The amount of peptide that prevents unwanted blood clots, however, will vary with the $IC_{50}$ of the peptide as well as with the half-life of the peptide in the body. The amount of peptide that prevents unwanted blood clots will also vary with the particular condition being treated, the age and physical condition of the subject being treated, the severity of the condition, the duration of the treatment, the nature of the concurrent therapy (if any), the specific route of administration and like factors within the knowledge and expertise of the health practitioner.

In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of peptides.

Thus, it will be understood that the peptide coagulation inhibitors of the invention can be used to inhibit blood clotting and thrombotic diseases in subjects at risk of developing such disorders.

WORKING EXAMPLES

The invention may be better understood by reference to the following examples, which serve to illustrate but not to limit the present invention.

Example 1

Synthesis of the L5S Peptide (SEQ ID NO. 12)

The peptide L5S (SEQ ID NO. 12), consisting of the amino acid sequence LDNFS (see FIG. 2), was synthesized using the solid-phase method using Fmoc chemistry in an Applied Biosystems (Foster City, Calif.) Model 431A Peptide Synthesizer. The activation was carried out with HBTU/DEA. The Nα-amino group was protected by Fmoc and side-chain functional groups were protected by t-Bu (D and S) and Trt (N). The peptide was cleaved with TFA/thioanisole/water/EDT (90:5:2.5:2.5) for 3.5 hours. About 50 mg of the crude peptide was obtained. HPLC chromatograms were obtained using a gradient of 5 to 60% Buffer B over 45 minutes (Buffer A: 0.1% TFA in water, Buffer B: 0.08% TFA in acetonitrile). The column used was a $C_{18}$ reverse phase column.

Fractions from the HPLC column that contained the peptide were collected, lyophilized and stored as a dry powder at −70° C. in a dessicator until it was ready to be used. Fifty mg of crude material yielded 40 mg of purified peptide at a purity of 95%.

Example 2

Assay of the N42R Peptide for Inhibition of Blood Clotting

In this study, a 42 amino acid peptide, N42R, encompassing amino acids 307–348 of human factor Va (FIG. 2, SEQ ID NO. 2) was synthesized using the method described in Example 1 and tested for its ability to inhibit prothrobminase activity using an assay whose endpoint was formation of a visual blood clot.

Each visual blood clotting reaction comprised three components. The first component was a thromboplastin reagent. Thromboplastin reagent refers to a reagent that contains phospholipids and tissue factor ("TF"). TF is a membrane protein that forms a complex with factors VII and VIIa, promotes conversion of factor VII to factor VIIa, which subsequently converts factor X to factor Xa (see FIG. 1). The thromboplastin reagent used was Simplastin Excel which was made by Organon Teknica (West Chester, Pa.) and is made from rabbit brain.

The second component of the visual clotting assay was plasma (the liquid part of the blood, containing blood clotting factors), which was immunodepleted of factor V using antibodies against factor V. Mixture of the thromboplastin reagent with the immunodepleted plasma did not result in coagulation. To obtain coagulation, the third component, containing factor V, was added. Addition of the third component was performed by adding normal (not immunodepleted) plasma to the reaction. The endpoint of the clotting reaction was visualization of a fibrin clot. By diluting the normal plasma before addition to the reaction, it was possible to adjust the time required for clotting to occur.

To test the ability of N42R to inhibit the clotting reaction, assays were set up by adding 100 µl of thromboplastin reagent (Simplastin Excel made by Organon Teknica) to 50 µl of human plasma which had been depleted of factor V/Va using antibodies specific for factor V/Va. The factor V/Va depleted plasma was added to the tube of thromboplastin while rocking the tube at 37° C. A dilution of factor Va was then added as described below.

Factor Va was purchased or, alternatively was produced by treatment of 50 nM of purified factor V (Haematologic Technologies, Inc.) with 1 nM α-thrombin for 10 min followed by the addition of 2 nM hirudin. An amount of the factor Va was then diluted in a $Ca^{2+}$-containing buffer to a concentration of 0.1–1 nM (in 50 µl) and added to the reaction such that a visible clot formed in approximately 25 seconds. This time was arbitrarily determined to be 100% activity.

Additional clotting reactions were then set up such that different concentrations of the peptides N42R peptide was present. A control, 24 amino acid peptide, D13R, encompassing amino acids 686–709 of human factor Va (FIG. 2, SEQ ID NO. 17) was also used in separate reactions. Clotting times longer than 25 seconds reflected inhibition of factor Va activity by the peptides. The results were plotted as percent of control prothrombinase activity as a function of peptide concentration.

The data (FIG. 3) show that the N42R peptide was a potent, dose-dependent inhibitor of prothrombinase clotting activity with an $IC_{50}$ of approximately 1.3 µM. The D13R peptide, on the other hand, did not inhibit prothrombinase activity even at concentrations as high as 250 µM.

Example 3

Assay of the AP4 Peptide for Inhibition of Prothrombinase Activity

In this study, a 10 amino acid peptide, AP4, encompassing amino acids 322–331 of human factor Va (see FIG. 2, SEQ ID NO. 6) was synthesized using the method described in Example 1 and tested for its ability to inhibit prothrobminase activity in a fluorescence assay.

The fluorescence assay specifically measured the conversion of prothrombin to α-thrombin, one essential reaction of the many required for blood clotting (see FIG. 1). This assay employed a reagent, called dansylarginine-N-(3-ethyl-1,5-pentanediyl)amide (also called "DAPA") (Nesheim, et al., 1979, Biochemistry, 18:996–1003), which bound to α-thrombin. DAPA was obtained from Haematologic Technologies, Inc. (Essex Junction, Vt.).

The fluorescent properties of DAPA were contributed by the dansyl moiety. When bound to α-thrombin, the fluorescence intensity and lifetime of the dansyl moiety were increased three-fold. Therefore, in this assay, when prothrombinase activity was uninhibited, α-thrombin was produced (see FIG. 1) and DAPA fluorescence was high. When prothrombinase activity was inhibited, as in the presence of peptide prothrombinase inhibitors, α-thrombin was not produced and DAPA fluorescence was low.

In a typical assay, the final concentrations of reagents were as follows: prothrombin, 1.4 µM; factor Xa, 10 nM; factor Va, 1 nM; phospholipid vesicles, 20 µM; DAPA, 3 µM; peptide, 100 µM. The buffer used was composed of 20 mM Hepes, 0.15 M NaCl, 5 mM $CaCl_2$, pH 7.4 [HBS ($Ca^{2+}$)]. Factors Va and Xa were obtained from Haematologic Technologies, Inc. Phospholipid vesicles were composed of 75% phosphatidylcholine (PC; from egg yolk; Sigma Chemical Co.; St. Louis, Mo.) and 25% phosphatidylserine (PS; from bovine brain; Sigma)

The phospholipid vesicles used in the above assay were prepared as described (Barenholz, et al., 1977, Biochemistry, 16:2806–10), a method incorporated herein by reference. Briefly, to make vesicles, solutions of PC and PS were mixed and dried under $N_2$ gas in a tube. A neutral buffer was added and the tube was sonicated, creating vesicles of a consistent size. After centrifugation to isolate the vesicles, the concentration of the vesicles was determined by phosphorus assay (Gomori, 1942, J Lab Clin Med, 27:955–60).

To set up the fluorescent assay, a first mixture containing prothrombin, factor Va, phospholipid vesicles and DAPA was made and incubated in the dark for 20 min. A second mixture, containing factor Xa and AP4 peptide was mixed and then added to the first mixture in a cuvette. Baseline fluorescence was monitored for 15 sec at room temperature using a Perkin Elmer MPF-44A fluorescence spectrophotometer with $\lambda_{ex}=280$ nm, $\lambda_{e}=550$ nm and a 500 nm long pass filter in the emission beam. The initial rates of α-thrombin formation were calculated from the baseline fluorescence measurements.

Control fluorescent prothrombinase reactions were also set up. One control reaction contained no peptide. The value for prothrombinase activity in this control was assigned a value of 100%. A second control reaction contained no peptide and no factor Va. The fluorescence in the no peptide, no factor Va reaction was background fluorescence.

The AP4 peptide was an efficient inhibitor of the prothrombinase reaction (see FIG. 4). AP4 decreased prothrombinase activity to approximately 1% of the level obtained with no peptide (the no peptide control reaction is labeled "Xa/Va" in FIG. 4; the no peptide, no factor Va reaction is labeled "Xa" in FIG. 4).

To determine the $IC_{50}$ of the AP4 peptide a series of fluorescent prothrombinase reactions was set up where each reaction had a different concentration of AP4 peptide. Using this series of reactions, concentrations of AP4 peptide spanning a concentration of from 100 nM to 200 µM were tested. The concentration of peptide at which prothrombinase activity was 50% of the activity in the absence of peptide (the $IC_{50}$) was found to be approximately 5 µM.

Example 4

Assay of Additional 10 Amino Acid Peptides, Spanning Amino Acids 307 to 356 of Human Factor Va, for Inhibition of Prothrombinase Activity In addition to AP4, nine additional overlapping peptides that spanned the amino acid region 307–356 of the heavy chain of factor Va (AP1–AP3 and AP5–AP9, FIG. 2) were synthesized using the method described in Example 1. These peptides were tested for inhibition of prothrombinase in the fluorescent assay, described in Example 3, All peptides spanning the region 307–356 of the factor Va heavy chain were able to inhibit activity to some degree (see FIG. 4). In addition to AP4, three other peptides spanning the 322–341 region of human factor Va were efficient inhibitors of the prothrombinase reaction. AP3 (amino acids 317–326 of human factor Va; SEQ ID NO. 5) decreased prothrombinase activity to approximately 38% of the no peptide level. AP5 (amino acids 327–336) decreased prothrombinase activity to approximately 8% of the no peptide level. AP6 (amino acids 332–341) decreased prothrombinase activity to approximately 48% of the no peptide level. The AP6 peptide had an $IC_{50}$ of approximately 30 µM.

Peptide AP9 (SEQ ID NO. 11), encompassing region 347–356 (FIG. 2) was also found to efficiently inhibit prothrombinase activity (FIG. 4). AP9 decreased prothrombinase activity to approximately 5% of the no peptide level. Because the adjacent, overlapping peptide, AP8 (SEQ ID NO. 10) had little inhibitory activity (approximately 80% prothrombinase activity of the no peptide control), the activity of AP9 was suspected to come from the region of AP9 that did not overlap AP8 (i.e., amino acids 352–356; see FIG. 2). Therefore, an additional peptide was synthesized and tested. L5S (SEQ ID NO. 12), a pentapeptide encompassing amino acid region 352–356 of the factor Va heavy chain was made. P15H (SEQ ID NO. 13), encompassing amino acid region 337–351, was also made and used as a negative control (FIG. 2).

These peptides were tested for inhibition of prothrombinase using the fluorescent assay described in Example 3. $IC_{50}$ was calculated by setting up a series of reactions to measure prothrombinase activity. To the individual reactions were added different concentrations of L5S or P15H. For each reaction, prothrombinase activity was determined by measuring DAPA fluroescence. The data were plotted (FIG. 5) as the percentage of maximum prothrombinase activity (y-axis) versus the concentration of the inhibitory peptide (x-axis). The peptide concentration at which prothrombinase activity was 50% of the maximum activity was the $IC_{50}$ of that inhibitory peptide. The data demonstrated that L5S was a potent inhibitor of factor Va cofactor activity, with an $IC_{50}$ of approximately 50 µM (FIG. 5). The P15H peptide did not inhibit prothrombinase even at concentrations of approximately 500 µM (FIG. 5).

Example 5

Assay of the EYFAE Pentapeptide (SEQ ID NO. 13) for Inhibition of Prothrombinase Activity In this study, a 5 amino acid peptide with the amino acid sequence EYFAE (SEQ ID NO. 13, see FIG. 2), which includes amino acids 323–325 of the human factor Va heavy chain (EYF) plus two additional amino acids (AE) attached to the C-terminal end of EYF, was synthesized using the method described in Example 1.

The EYFAE pentapeptide was tested for its ability to inhibit prothrobminase activity in the fluorescent assay described in Example 3 (see FIG. 6). A series of fluorescent prothrombinase reactions was set up and different concentrations of EYFAE were added to each reaction.

The data were displayed (see FIG. 6) as the percentage of maximum prothrombinase activity (y-axis) versus the concentration of the inhibitory peptide (x-axis). The peptide concentration at which prothrombinase activity was 50% of the maximum activity was the $IC_{50}$ of that inhibitory peptide. The data demonstrated that the EYFAE pentapeotide was a potent inhibitor of factor Va cofactor activity, with an $IC_{50}$ of approximately 10–15 µM.

It should be understood that the preceding is merely a detailed description of preferred embodiments. It therefore should be apparent to those of ordinary skill in the art that various modifications and equivalents can be made without departing from the spirit and scope of the invention. All references, patents and patent publications that are identified in this application are incorporated in their entirety herein by reference. The specific examples presented below are illustrative only and is not intended to limit the scope of the invention described herein.

We claim:

1. A method for treating human subjects with blood clotting disorders, comprising:
   administering a pharmaceutical composition to the human subjects,
   wherein the pharmaceutical composition comprise a peptide having a total length of from 3 to 10 amino acids,
   wherein said peptide comprises a sequence which is identical to a sequence of from 3 to 10 consecutive amino acids found within amino acids 16 to 25 or 46 to 50 of (SEQ ID No: 1), wherein SEQ ID No: 1 represents amino acids 307 to 356 of the human blood clotting factor Va, and
   wherein the peptide exhibits an $IC_{50}$ of between 50 nM to 500 μM for inhibition of prothrombinase.

2. The method of claim 1 wherein the peptide comprises at least 5 amino acids which are identical to a sequence of consecutive amino acids found within amino acids 16 to 25 or 46 to 50 of (SEQ ID No: 1), wherein SEQ ID No: 1 represents amino acids 307 to 356 of the human blood clotting factor Va.

3. The method of claim 1 wherein the peptide comprises at least 7 amino acids which are identical to a sequence of consecutive amino acids found within amino acids 16 to 25 of (SEQ ID No: 1), wherein SEQ ID No: 1 represents amino acids 307 to 356 of the human blood clotting factor Va.

4. The method of claim 1 wherein the peptide comprises at least 10 amino acids which are identical to a sequence of consecutive amino acids found within amino acids 16 to 25 of (SEQ ID No: 1), wherein SEQ ID No: 1 represents amino acids 307 to 356 of the human blood clotting factor Va.

5. The method of claim 1, wherein the sequence of thea peptide is selected from the group consisting of SEQ ID No: 6 and SEQ ID No: 12.

6. The method of claim 1, wherein at least one amino acid within said peptide is a non-naturally occurring amino acid.

7. The method of claim 1, wherein at least one amino acid within said peptide is a D-amino acid.

8. The method of claim 1, wherein at least two amino acids in said sequence are joined by non-hydrolyzable peptide bonds.

9. The peptide of claim 1, wherein said peptide is a cyclized peptide.

* * * * *